United States Patent
Early

(10) Patent No.: US 8,987,341 B2
(45) Date of Patent: Mar. 24, 2015

(54) PROCESS FOR IMPROVING THE HYDROGEN CONTENT OF A SYNTHESIS GAS

(75) Inventor: Simon Robert Early, London (GB)

(73) Assignee: Davy Process Technology Limited, Greater London (GB)

( * ) Notice: Subject to any disclaimer, the term of this patent is extended or adjusted under 35 U.S.C. 154(b) by 0 days.

(21) Appl. No.: 13/989,442

(22) PCT Filed: Nov. 22, 2011

(86) PCT No.: PCT/GB2011/052291
§ 371 (c)(1),
(2), (4) Date: Jun. 25, 2013

(87) PCT Pub. No.: WO2012/069821
PCT Pub. Date: May 31, 2012

(65) Prior Publication Data
US 2014/0058002 A1    Feb. 27, 2014

(30) Foreign Application Priority Data

Nov. 24, 2010 (GB) .................................. 1019940.4

(51) Int. Cl.
*C07C 27/00* (2006.01)
*C07C 29/151* (2006.01)
(Continued)

(52) U.S. Cl.
CPC ............... *C07C 29/1516* (2013.01); *C01B 3/34* (2013.01); *C01B 3/503* (2013.01); *C07C 29/1518* (2013.01); *C10G 2/30* (2013.01); *C10K 1/32* (2013.01); *C10K 3/04* (2013.01);
(Continued)

(58) Field of Classification Search
USPC .......................................... 518/700, 702–705
See application file for complete search history.

(56) References Cited

U.S. PATENT DOCUMENTS 1,330,772 A    2/1920   Bosch et al.
1,809,978 A    6/1931   Larson
(Continued)

FOREIGN PATENT DOCUMENTS

EP    0123534 A2    10/1984
EP     195200 A2     9/1986
(Continued)

OTHER PUBLICATIONS

International Preliminary Report on Patentability issued on Jun. 6, 2013, in PCT/GB2011/052291, 9 pages.
(Continued)

*Primary Examiner* — Jafar Parsa
(74) *Attorney, Agent, or Firm* — Senniger Powers LLP

(57) ABSTRACT

A process for improving the hydrogen content of a synthesis gas stream to a synthesis loop, comprising the steps of: (a) removing a purge stream comprising hydrogen and hydrocarbons from a synthesis loop; (b) separating hydrogen from the purge stream; (c) passing the purge stream to a reformer and reacting with steam and oxygen to produce a stream comprising hydrogen and carbon monoxide; (d) subjecting the reformed reaction product stream to a shift reaction to produce a stream comprising carbon dioxide and hydrogen; (e) subjecting the product stream from the shift reaction to separation to separate hydrogen from carbon dioxide; (f) supplying the separated hydrogen to the synthesis loop; and (g) removing the carbon dioxide.

13 Claims, 3 Drawing Sheets

(51) Int. Cl.
  *C01B 3/34* (2006.01)
  *C01B 3/50* (2006.01)
  *C10G 2/00* (2006.01)
  *C10K 1/32* (2006.01)
  *C10K 3/04* (2006.01)

(52) U.S. Cl.
  CPC . *C01B2203/0238* (2013.01); *C01B 2203/0244* (2013.01); *C01B 2203/0283* (2013.01); *C01B 2203/0405* (2013.01); *C01B 2203/043* (2013.01); *C01B 2203/0475* (2013.01); *C01B 2203/0495* (2013.01); *C01B 2203/061* (2013.01); *C01B 2203/062* (2013.01); *C01B 2203/148* (2013.01)
  USPC ........... 518/700; 518/702; 518/703; 518/704; 518/705

(56) References Cited

U.S. PATENT DOCUMENTS

| | | | |
|---|---|---|---|
| 4,226,795 A | 10/1980 | Bowman | |
| 4,546,111 A * | 10/1985 | Banquy | 518/703 |
| 4,888,130 A | 12/1989 | Banquy | |
| 5,496,859 A | 3/1996 | Fong et al. | |
| 7,220,505 B2 | 5/2007 | Malhotra et al. | |
| 2010/0056648 A1 | 3/2010 | Schroer et al. | |
| 2010/0317903 A1* | 12/2010 | Knuuttila | 585/14 |

FOREIGN PATENT DOCUMENTS

| | | |
|---|---|---|
| EP | 1230203 B1 | 2/2004 |
| WO | 2007045966 A2 | 4/2007 |
| WO | 2008122399 A1 | 10/2008 |
| WO | 2009059936 A2 | 5/2009 |

OTHER PUBLICATIONS

International Search Report, PCT/GB2011/052291, dated Feb. 16, 2012, 3 pages.

Written Opinion, PCT/GB2011/052291, dated Feb. 16, 2012, 7 pages.

* cited by examiner

PROCESS FOR IMPROVING THE HYDROGEN CONTENT OF A SYNTHESIS GAS

REFERENCE TO RELATED APPLICATIONS

This application is a United States National Stage Application based on International Application No. PCT/GB2011/052291, filed Nov. 22, 2011, and claims the benefit of United Kingdom Patent Application No. 1019940.4, filed Nov. 24, 2010, the entire contents of which are incorporated herein by reference.

The present invention relates to a method for adjusting the ratio of hydrogen to carbon monoxide in synthesis gas.

Synthesis gas can be produced by a variety of methods. In some arrangements a gasifier is used to produce the synthesis gas from, for example, coal or biomass. Such gasifiers produce synthesis gas with a fixed total of hydrogen and carbon monoxide. In an ideal system the hydrogen and carbon monoxide will be produced in stoichiometric ratio. However, as systems are not generally ideal the ratio of hydrogen to carbon monoxide is not generally stoichiometric. Depending on the gasifier design the synthesis gas will also contain significant levels of inerts such as nitrogen as well as a significant hydrocarbon content. Usually, the hydrocarbon content is primarily methane but $C_2$ compounds may also be present.

Synthesis gas is useful in a variety of reactions. For example, it is used as a starting material in the production of methanol. For maximum methanol make, the R ratio of the feed synthesis gas should be close to 2 where $R=(H_2-CO_2)/(CO+CO_2)$. Typically, where the synthesis gas feed has a low R ratio which occurs because a gasifier commonly makes synthesis gas with a stoichiometric surplus of carbon monoxide, a purge is taken from the methanol synthesis loop. Hydrogen is then separated from this purge and recycled to the methanol synthesis loop to counter the problems associated with the low R ratio. The remaining carbon-rich stream is rejected and sent to the fuel system. The carbon-rich stream will typically contain hydrocarbons as well as nitrogen and other inerts. Examples of these conventional processes can be found in U.S. Pat. No. 4,226,795 and WO2007/045966.

Whilst this approach goes some way towards addressing the problems associated with the low R ratio of the synthesis gas, there is still a need for improved processes. Generally activity has concentrated on improving the ratio of carbon monoxide and hydrogen in the synthesis gas feed to the methanol plant. Examples of such processes can be found in U.S. Pat. No. 5,496,859, U.S. Pat. No. 4,888,130, WO2008/122399, EP1230203 and U.S. Pat. No. 7,220,505. In these processes the feed stream of synthesis gas is subjected to a reforming reaction to convert any hydrocarbon present to hydrogen. Whilst these processes improve the R ratio they do suffer from certain disadvantages and drawbacks. In particular, they require large reforming reactors and associated equipment which increases both capital and operating costs.

EP195200 describes a process in which the purge gas from the methanol synthesis is subjected to catalytic reforming and then to a carbon monoxide conversion. A pressure-swing adsorption unit is used to separate the converted gas into hydrogen and inerts.

It has now been discovered that an improved process can be provided where the hydrocarbon content of the purge from the synthesis loop has hydrogen removed before being subjected to a reforming reaction to produce additional hydrogen which is recycled to the synthesis loop. This raises the R ratio of the synthesis gas fed to the synthesis loop. Nitrogen and other inerts which may be present in the purge may be removed in a waste fuel stream. Generally it would be expected that reforming the purge stream from a reaction loop would result in an unacceptably high build-up of inerts. However, the process of the present invention enables this problem to be overcome.

According to the present invention there is provided a process for improving the hydrogen content of a synthesis gas stream to a synthesis loop, comprising the steps of:
(a) removing a purge stream comprising hydrogen and hydrocarbons from a synthesis loop;
(b) separating hydrogen from the purge stream;
(c) passing the purge stream to a reformer and reacting with steam and oxygen to produce a stream comprising hydrogen and carbon monoxide;
(d) subjecting the reformed reaction product stream to a shift reaction to produce a stream comprising carbon dioxide and hydrogen;
(e) subjecting the product stream from the shift reaction to separation to separate hydrogen from carbon dioxide;
(f) supplying the separated hydrogen to the synthesis loop; and
(g) removing the carbon dioxide.

Subjecting the hydrocarbon content of the purge stream to the reforming step of the present invention enables additional hydrogen to be generated and returned to the synthesis loop to improve the hydrogen content of the synthesis gas stream. This results in increased production of desired product of the reaction being carried out in the synthesis loop. Thus, for example, where a synthesis gas with an R of less than 2 being used in the production of methanol, treating the purge gas in accordance with the present invention and returning the hydrogen to the methanol synthesis loop will result in increased methanol production. In addition there will be a minimum loss of carbon via the purge stream thereby increasing the overall carbon efficiency.

The presence of the separation step (b) enables an improved process to be achieved.

Further as the flow rate of a purge stream from a synthesis loop will be lower than the flow rate of the synthesis gas feed to the synthesis loop, the size of equipment required for the reforming reaction of the present invention is substantially less than that in the prior art arrangements in which the feed is subjected to reforming.

The synthesis gas supplied to the reaction loop from which the purge is taken may have any suitable composition. As the process of the present invention enables hydrogen to be obtained from any hydrocarbon present, the gas may have a relatively high hydrocarbon content. Generally a hydrocarbon content of 4% or above may be used.

The synthesis gas will generally also include inerts such as nitrogen and thus the purge stream will also comprise inerts. The process of the present invention enables inerts to be effectively handled in that the inerts will pass through the process of the present invention with the carbon components and will be removed with the carbon dioxide. As the inerts can be effectively handled, the synthesis gas may have a relatively high inert content. Thus it may have 1% or more of inerts. Indeed it may even have 4% or more of inerts.

The process of the present invention may be utilised in a variety of reactions. In general it is applicable to any process in which a synthesis gas having less than a stoichiometric hydrogen content is used as feed and where hydrocarbons will be present in the purge. The process is particularly applicable to the process for the production of methanol. It is also useful in other processes such as Fischer-Tropsch processes. Generally these reactions are ones in which inert content will build up and thus the inert content in the purge may be of about 10% or more.

The purge supplied to the process of the present invention will generally contain a substantial part of the hydrocarbons, and where present, the inerts, in the original feed. It may be about 90% or more of the hydrocarbons, and where present, the inerts, in the original feed.

In the separation in step (b), hydrogen is separated from the purge stream. The separated hydrogen may be recycled to the synthesis loop, the remaining stream which contains the hydrocarbon, is passed on to the reforming reaction.

The separation of the hydrogen from the purge stream in step (b) may be carried out by any suitable means. In one arrangement a membrane separation technique may be used. In an alternative arrangement pressure swing adsorption may be used.

In one alternative arrangement, the pressure of the stream containing the hydrocarbon will be reduced so it is just high enough to produce hydrogen at the required pressure to be supplied directly to the synthesis loop.

The oxygen reacted with the purge steam in the reformer may be supplied as an oxygen stream or as air. The use of air will offer the advantage of eliminating the requirement for an air separation unit. Whilst the use of air may result in a reduction in the hydrogen production of the process, the reduction will be small, generally of the order of less than 5%. The introduction of additional nitrogen to the system by the use of air is generally considered to be a drawback on commercial plants. However, as the process of the present invention enables the effective handling of inerts, the presence of additional nitrogen does not represent a significant problem as the nitrogen will be removed from the process with the carbon dioxide.

Any suitable amount of oxygen, whether supplied as pure oxygen or as air, may be used. However, in one arrangement it may be kept as low as possible to maximise the hydrogen production.

The reforming process may be carried out by any suitable means. In one arrangement an autothermal reformer is used. Any suitable reaction conditions may be used. In one arrangement the autothermal reformer will operate at from about 900 to about 1050° C. The reformer will generally be operated at a suitable pressure to be mixed back into the synthesis gas feed without further compression. Typically it will be at from about 20 to about 50 bara.

The stream removed from the reforming process will generally be cooled by any suitable means such that the stream is at the optimum temperature for the inlet temperature to the shift reaction. The shift reaction may be carried out in one stage or in a plurality of stages. The shift reaction may be carried out at any suitable conditions. The conditions selected will generally depend on the catalyst selected. Examples of suitable catalysts and the operating conditions therefor can be found in, for example U.S. Pat. No. 1,809,978 and U.S. Pat. No. 1,330,772 which are incorporated herein by reference. In some arrangements it may be operated at a temperature of about 350° C. inlet to about 450° C. exit temperature using an iron-based catalyst followed by a lower temperature shift may be carried out at about 200° C. inlet to about 450° C. exit using a copper/zinc catalyst. In one alternative arrangement, a single medium temperature shift stage may be used with, for example, a copper/zinc catalyst which operates at about 200° C. inlet to about 320° C. exit.

The separation in step (f) may be carried out by any suitable means. However, pressure swing adsorption is particularly preferred as it gives good hydrogen recovery and inerts rejection.

The hydrogen produced by the process of the present invention may be of any suitable purity. Whilst high purity, such as 99% or better, is not essential for methanol or Fischer-Tropsch reactions, the production of high purity hydrogen does offer certain advantages. Further it may be particularly desirable for other synthesis loops.

The hydrogen separated in step (f) may be supplied directly to the synthesis loop or it may be combined with the hydrogen removed in step (b) before being returned to the synthesis loop.

The carbon dioxide removed in step (g) may be treated as appropriate. In one arrangement it may be fed, with any inerts present, to the fuel system.

The process of the present invention may include heat recovery and cooling steps as required. In addition, the process may include a step of condensing water from the stream prior to the separation step (e).

As discussed above, the process of the present invention is particularly suitable for use with a process for the production of methanol. Thus according to a second aspect of the present invention there is provided a process for the production of methanol comprising:
  providing synthesis gas to a methanol synthesis loop;
  removing a purge stream from the methanol synthesis loop; and
  treating the purge stream in accordance with the above first aspect of the present invention.

For gasifier-based plants, the $H_2$+CO in the synthesis gas from the gasifier is fixed and the maximum possible methanol produced is approximately ($H_2$+CO)/3 at an R-value of 2.0. The production of extra hydrogen enables the production of methanol to be increased for a fixed size of gasifier.

The process of the present invention is also suitable for use with a Fischer-Tropsch process. Thus according to a third aspect of the present invention there is provided a process for carrying out Fischer-Tropsch reactions comprising:
  providing synthesis gas to a Fischer-Tropsch synthesis loop;
  removing a purge stream from the Fischer-Tropsch synthesis loop; and
  treating the purge stream in accordance with the above first aspect of the present invention.

In the above second and third aspects of the present invention, the recycle of the hydrogen from the reforming process enables the R-value of the synthesis gas feed to be adjusted to maximise the yield of the reaction.

The present invention will now be described with reference to the accompanying figure in which.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, and the like may be required in a commercial plant. The provision of such ancillary items of equipment forms no part of the present invention and is in accordance with conventional chemical engineering practice.

A purge is taken from a synthesis loop (not shown) and fed in line 1 to a membrane separator 2. The hydrogen separated will be returned to the feed to the synthesis loop in line 3. The remaining components of the purge stream which will comprise the hydrocarbons and the inerts are passed in line 4 to the autothermal reformer 5. Steam and oxygen, which may be supplied as air, are added in line 6. Hydrogen and carbon monoxide produced in the autothermal reformer 5 is passed in line 7 to a reactor 8 in which a shift reaction is carried out to produce hydrogen and carbon dioxide. This, together with any inerts, will then be passed in line 9 to the pressure swing absorption apparatus 10 to separate hydrogen from the carbon dioxide and inerts. The hydrogen is returned in line 11 to the synthesis loop. The carbon dioxide and any inerts present are removed in line 12 and may be used as fuel.

In an alternative arrangement, the separator prior to the autothermal reformer is omitted. Here the purge is supplied in line 1 to the autothermal reformer 5 where it is reacted with steam and oxygen (which may be provided as air) added in line 6. Hydrogen and carbon monoxide produced in the autothermal reformer 5 is passed in line 7 to a reactor 8 in which a shift reaction is carried out to produce hydrogen and carbon dioxide. This, together with any inerts, will then be passed in line 9 to the pressure swing absorption apparatus 10 to separate hydrogen from the carbon dioxide and inerts. The hydrogen is returned in line 11 to the synthesis loop. The carbon dioxide and any inerts present are removed in line 12 and may be used as fuel.

EXAMPLES

The present invention will now be described, by way of example, with reference to the following examples. In each of the Examples, the shift stage assumes a single medium temperature shift reactor. In each case the content of $H_2+CO$ in the synthesis gas from the gasifier is the same at 196449 $Nm^3/h$

Comparative Example 1

Figure 1:
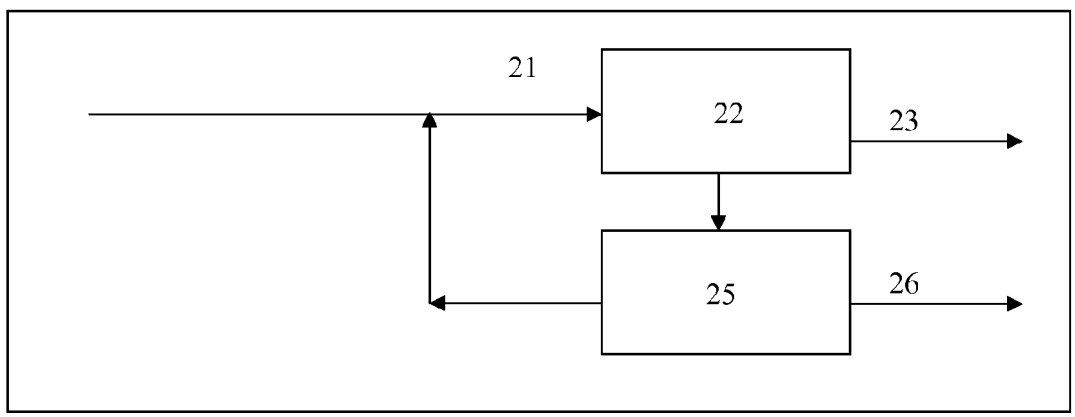
FIG. 1 is a flowsheet block diagram for the process of Comparative Example 1.

The flowsheet utilised in this Comparative Example is provided in FIG. 1. Syngas from the gasifier is supplied in line 21 to the synthesis loop 22. Crude product is removed in line 23. Unreacted gas is passed in line 24 to the separation step 25 which is carried out in a membrane separator. A purge is removed in line 26 and the remainder is recycled in line 27 to line 21. The composition of the various streams is as set out in Table 1.

Example 2

Figure 2:
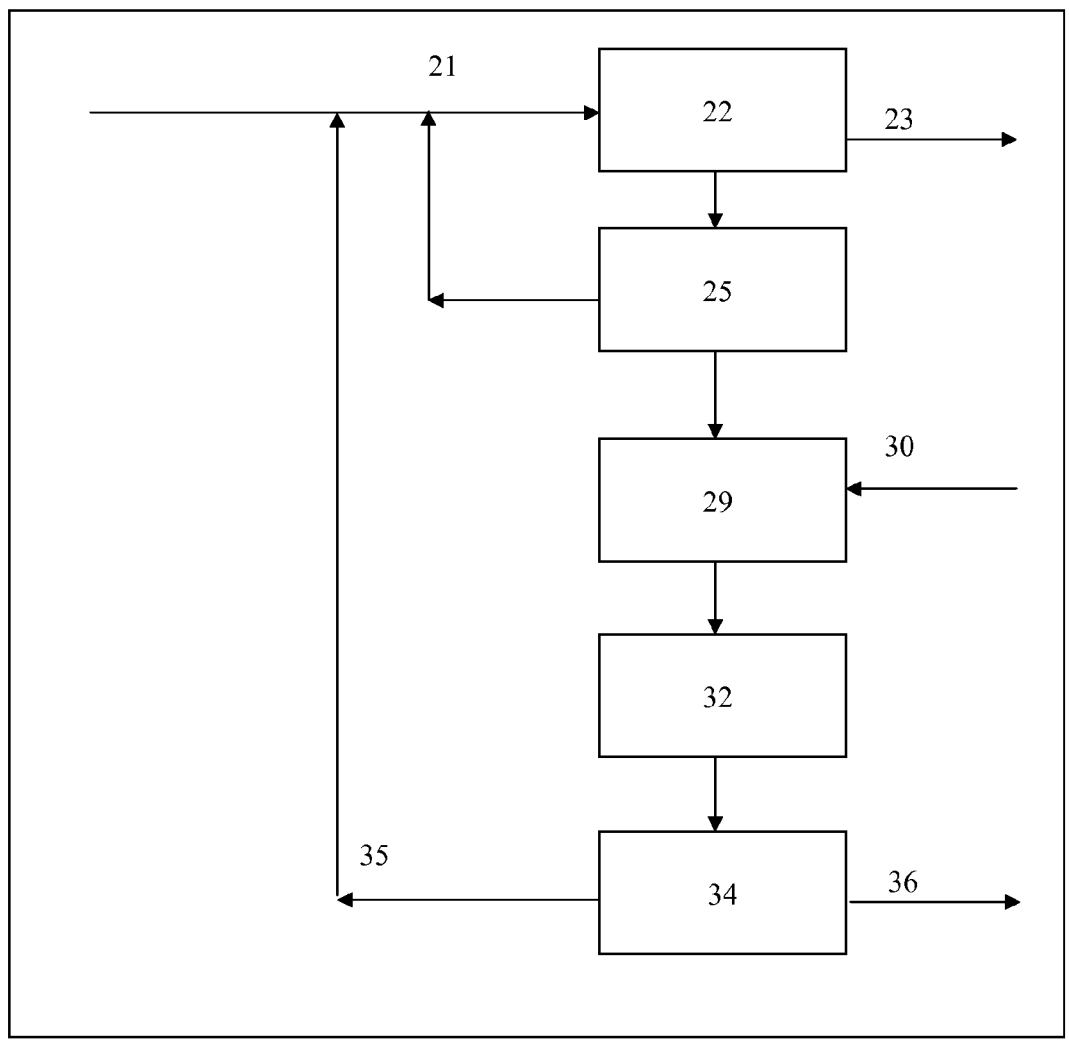
FIG. 2 is a flowsheet block diagram for the processes of Example 2 and 3.

The flowsheet utilised in this Example 2 is provided in FIG. 2. Here syngas from the gasifier is supplied in line 20. It is then combined with the recycled streams (discussed below) to form stream 21 which is supplied to the methanol synthesis loop 22. Crude product is removed in line 23. Unreacted gas is passed in line 24 to the separation step 25 which is carried out in a membrane separator. Separated hydrogen is returned to the methanol synthesis loop 22 in line 27. The remaining components are passed in line 28 to the autothermal reformer 29. Oxygen is supplied to the reformer in line 30. Hydrogen and carbon monoxide produced in the autothermal reformer is passed in line 31 to the reactor 32 in which the shift reaction will take place to produce hydrogen and carbon dioxide. This is then passed in line 33 to the pressure swing absorption apparatus 34 to separate the hydrogen from any inerts. The hydrogen is returned in line 35 to the synthesis loop and the carbon dioxide and any inerts are removed in purge stream 36. The composition of the various streams is as set out in Table 1.

The reaction conditions for Example 2 were as follows:

Methanol synthesis reactor 22 operates at about 22 bara, 270° C. exit the reactor.

Membrane separator 25: The recovery is "$Nm^3/h$ content of that component in stream 27" divided by "$Nm^3/h$ content of that component in stream 24". 75% hydrogen recovery. Other recoveries have been rounded. 20% CO recovery, 15% $CH_4$ recovery, 15% $N_2$ recovery, 80% $H_2O$, 50% methanol recovery.

Reformer 29 operates at about 33 bara, 975° C. exit the autothermal reactor.

Shift operates at about 31 bara, 315° C. exit the shift reactor

PSA 34 Stream 35=about 80% of the $H_2$ content of stream 33.

Example 3

Example 2 was repeated except that air is added in line 30 rather than oxygen. The composition of the various streams is as set out in Table 1.

Comparative Example 4

Figure 3:
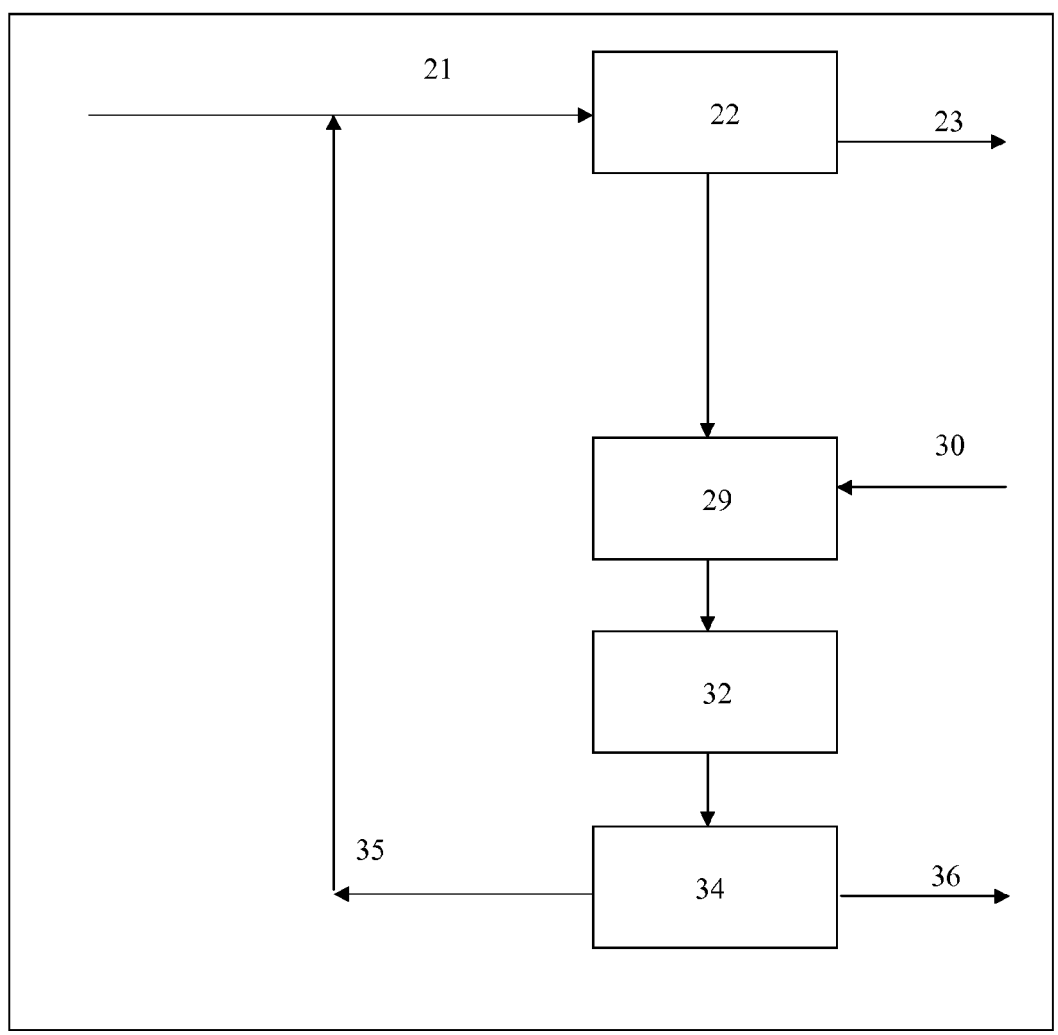
FIG. 3 is a flowsheet block diagram for the process of Comparative Example 4.

Example 2 was repeated without the separator step 25. The flowsheet is illustrated in FIG. 3.

The R-value of the synthesis gas to the methanol synthesis loop is the same for each of Examples 2, 3 and Comparative Example 4. It should be noted that for Example 1, the R-value of the syngas from the gasifier system must be just above the stoichiometric value of 2, which gives a slightly lower R-value to the methanol synthesis loop compared to the other examples.

It will be noted that in Comparative Example 4 the oxygen consumption is higher than in Example 2 but lower methanol production is achieved. Thus the benefit of the pressure of the separation step 25 can be seen.

TABLE 1

| | | Comparative Example 1 | Example 2 | Example 3 | Comparative Example 4 |
|---|---|---|---|---|---|
| Syngas From Gasifier System (stream 20) | Water | 0.10% | 0.10% | 0.10% | 0.10% |
| | Hydrogen | 62.37% | 58.94% | 59.47% | 59.79% |
| | CO | 26.54% | 29.97% | 29.44% | 29.12% |
| | CO2 | 3.00% | 3.00% | 3.00% | 3.00% |
| | Methane | 4.00% | 4.00% | 4.00% | 4.00% |
| | Nitrogen | 4.00% | 4.00% | 4.00% | 4.00% |
| | Total flow ($Nm^3/h$) | 220950 | 220950 | 220950 | 220950 |
| | R-value | 2.010 | 1.697 | 1.741 | 1.768 |

TABLE 1-continued

|  |  | Comparative Example 1 | Example 2 | Example 3 | Comparative Example 4 |
|---|---|---|---|---|---|
| Syngas To Methanol Synthesis Loop (stream 21) | Water | 0.11% | 0.10% | 0.10% | 0.08% |
|  | Hydrogen | 64.63% | 66.35% | 66.35% | 66.82% |
|  | CO | 23.89% | 23.73% | 23.73% | 24.03% |
|  | $CO_2$ | 2.96% | 2.55% | 2.55% | 2.47% |
|  | Methane | 4.11% | 3.57% | 3.57% | 3.30% |
|  | Nitrogen | 4.29% | 3.70% | 3.70% | 3.30% |
|  | Total flow ($Nm^3/h$) | 247650 | 280780 | 276687 | 267760 |
|  | R-value | 2.296 | 2.428 | 2.428 | 2.428 |
| Oxygen source to Reformer (stream 30) | N2 + Ar ($Nm^3/h$) | NIL | 1 | 1052 | 1 |
|  | Oxygen ($Nm^3/h$) | NIL | 279 | 279 | 335 |
| From Reformer (stream 35) | Hydrogen ($Nm^3/h$) | NIL | 26450 | 22890 | 46810 |
| Crude product (stream 23) | Methanol ($Nm^3/h$) | 61561 | 69609 | 68497 | 67510 |
|  | Efficiency | 94.01% | 106.30% | 104.60% | 103.10% |

= 3 × Methanol/(H2 + CO) from gasifier

The invention claimed is:

1. A process for improving the hydrogen content of a synthesis gas stream to a synthesis loop, comprising the steps of:
   (a) removing a purge stream comprising hydrogen and hydrocarbons from a synthesis loop;
   (b) separating hydrogen from the purge stream;
   (c) passing the purge stream to a reformer and reacting with steam and oxygen to produce a stream comprising hydrogen and carbon monoxide;
   (d) subjecting the reformed reaction product stream to a shift reaction to produce a stream comprising carbon dioxide and hydrogen;
   (e) subjecting the product stream from the shift reaction to separation to separate hydrogen from carbon dioxide;
   (f) supplying the separated hydrogen to the synthesis loop; and
   (g) removing the carbon dioxide.

2. A process according to claim 1 wherein the purge stream additionally comprises inerts.

3. A process according to claim 1 wherein the separated hydrogen is recycled to the synthesis loop.

4. A process according to claim 1 wherein the separation in step (b) is carried out by membrane separation.

5. A process according to claim 1 wherein the oxygen reacted with the purge stream in the reformer is supplied as air.

6. A process according to claim 1 wherein the reforming process is carried out in an autothermal reformer.

7. A process according to claim 6 wherein the autothermal reformer will operate at from about 900 to about 1050° C.

8. A process according to claim 6 wherein the reformer operates at a pressure of from about 20 to about 50 bara.

9. A process according to claim 1 wherein the separation in step (f) is carried out by pressure swing adsorption.

10. A process according to claim 1 wherein the hydrogen separated in step (f) is supplied directly to the synthesis loop or is combined with the hydrogen removed in step (b), where present, before being returned to the synthesis loop.

11. A process according to claim 1 wherein the carbon dioxide removed in step (g) is fed, with any inerts present, to the fuel system.

12. A process for the production of methanol comprising:
   providing synthesis gas to a methanol synthesis loop;
   removing a purge stream from the methanol synthesis loop; and
   treating the purge stream in accordance with claim 1.

13. A process for carrying out Fischer-Tropsch reactions comprising:
   providing synthesis gas to a Fischer-Tropsch synthesis loop;
   removing a purge stream from the Fischer-Tropsch synthesis loop; and
   treating the purge stream in accordance with claim 1.

* * * * *